United States Patent
Brower et al.

[11] Patent Number: 6,104,482
[45] Date of Patent: Aug. 15, 2000

[54] CONTAINER FINISH CHECK DETECTION

[75] Inventors: Dennis L. Brower, Sand Creek, Mich.;
James A. Ringlien, Maumee, Ohio;
John W. Juvinall, Ottawa Lake, Mich.;
William H. Anderson, Sylvania, Ohio

[73] Assignee: Owens-Brockway Glass Container Inc., Toledo, Ohio

[21] Appl. No.: 09/453,761

[22] Filed: Dec. 2, 1999

[51] Int. Cl.[7] .................................................. G01N 21/00
[52] U.S. Cl. ................................ 356/239.4; 356/239.7; 356/239.1; 356/240.1; 356/428
[58] Field of Search .......................... 356/239.4, 239.7, 356/239.1, 240.1, 237.1, 428, 426; 250/223 B

[56] References Cited

U.S. PATENT DOCUMENTS

| | | |
|---|---|---|
| 2,286,836 | 6/1942 | Sachtleben . |
| 3,030,516 | 4/1962 | Seavey . |
| 3,171,033 | 2/1965 | Mathias et al. . |
| 3,176,842 | 4/1965 | Fry . |
| 3,262,561 | 7/1966 | Sorbie . |
| 3,287,564 | 11/1966 | Gore et al. . |
| 3,292,785 | 12/1966 | Calhoun . |
| 3,505,526 | 4/1970 | Sendt . |
| 3,727,068 | 4/1973 | Poynton et al. . |
| 3,894,806 | 7/1975 | Remy et al. . |
| 3,963,348 | 6/1976 | Nakatani et al. . |
| 4,208,130 | 6/1980 | Saconney et al. . |
| 4,230,219 | 10/1980 | Pezzin et al. . |
| 4,378,493 | 3/1983 | Dorf et al. . |
| 4,606,634 | 8/1986 | Bieringer . |
| 4,915,237 | 4/1990 | Chang et al. . |
| 4,945,228 | 7/1990 | Juvinall et al. ........................... 356/240 |
| 5,200,801 | 4/1993 | Juvinall et al. . |
| 5,442,446 | 8/1995 | Gerber et al. . |
| 5,495,330 | 2/1996 | Champaneri et al. . |
| 5,592,286 | 1/1997 | Fedor . |
| 5,633,721 | 5/1997 | Mizutani . |
| 5,637,864 | 6/1997 | Nicks et al. . |
| 5,753,905 | 5/1998 | Ringlien ................................... 356/240 |
| 5,844,677 | 12/1998 | Dimmick, Sr. et al. ................ 356/240 |
| 5,900,945 | 5/1999 | Hinata et al. . |

*Primary Examiner*—Frank G. Font
*Assistant Examiner*—Roy M. Punnoose

[57] ABSTRACT

Apparatus for detecting checks in the finish of a translucent container that includes a first optical subassembly in which a first light source directs light energy onto the container finish as it rotates and a first light sensor receives portions of the first light energy reflected from horizontal checks in the container finish, and second and third optical subassemblies include respective second and third light sources and associated second and third sensors for directing light energy onto the container finish and receiving energy reflected from vertical checks in the container finish. Each optical subassembly includes an associated mounting plate, by means of which the optical subassemblies are mounted at an inspection station with the first light source and sensor disposed in a vertical plane, and the second and third light sources and sensors disposed in opposed mirror-image arrays on opposite sides of the vertical plane. The mounting plates include interlocking pins and slots that are configured for simultaneous adjustment of all optical subassemblies to accommodate container finishes of differing diameter.

52 Claims, 13 Drawing Sheets

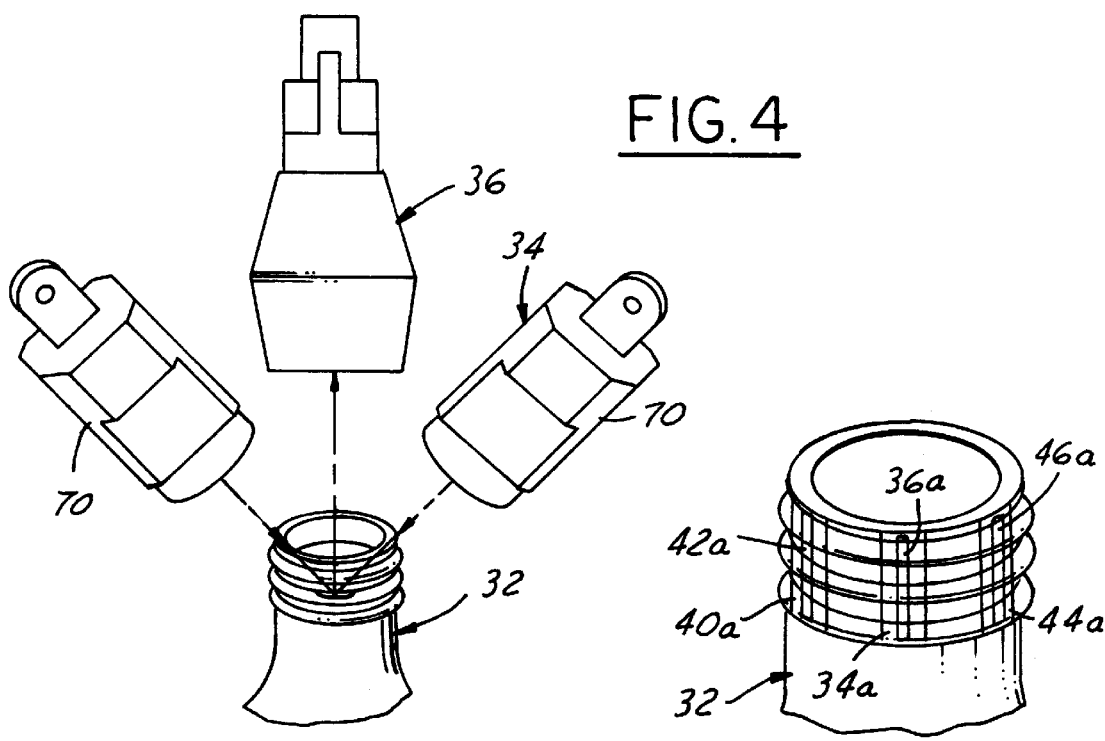
FIG. 4
FIG. 5
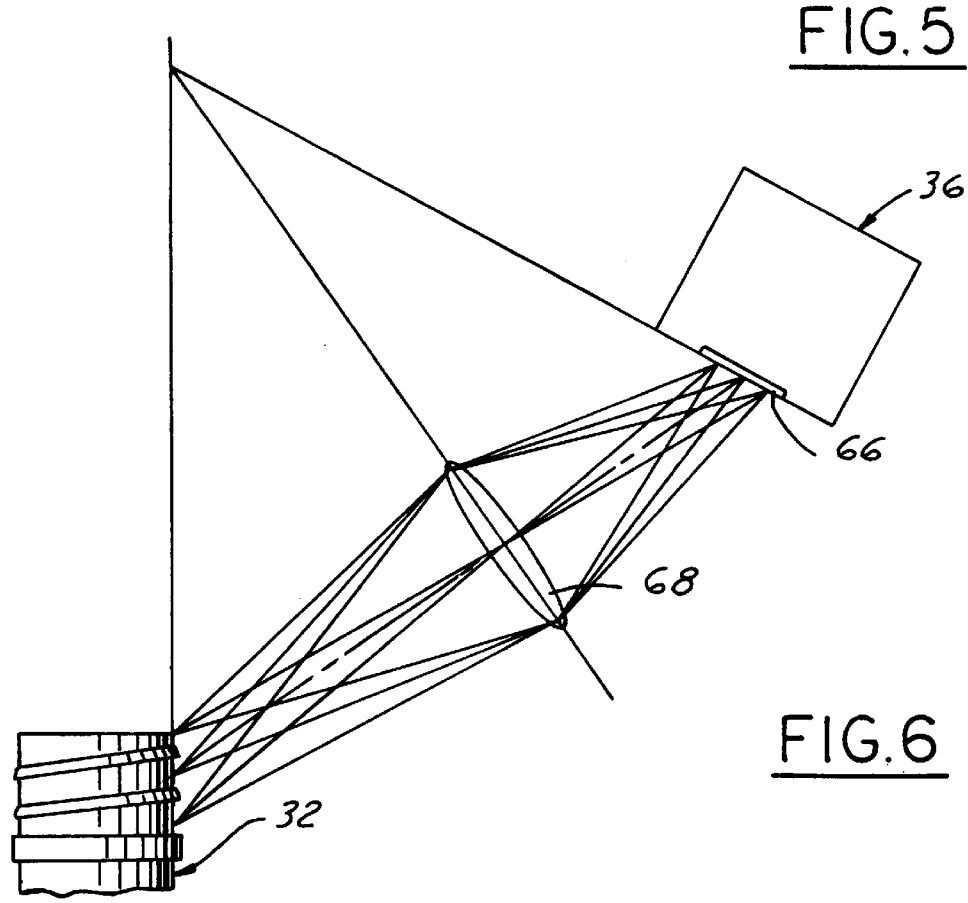
FIG. 6

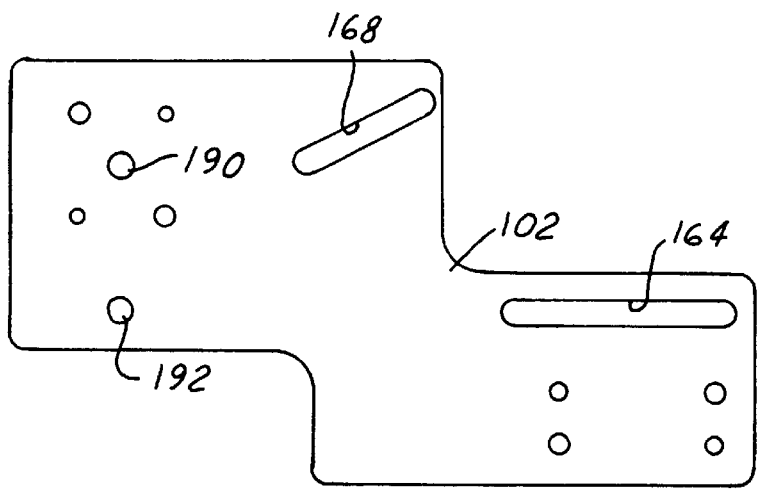
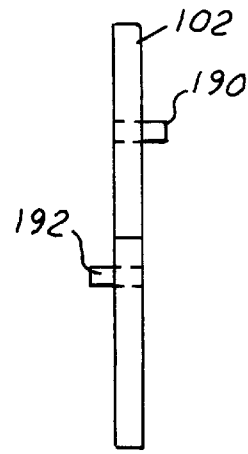
FIG.22　　　　　　FIG.23
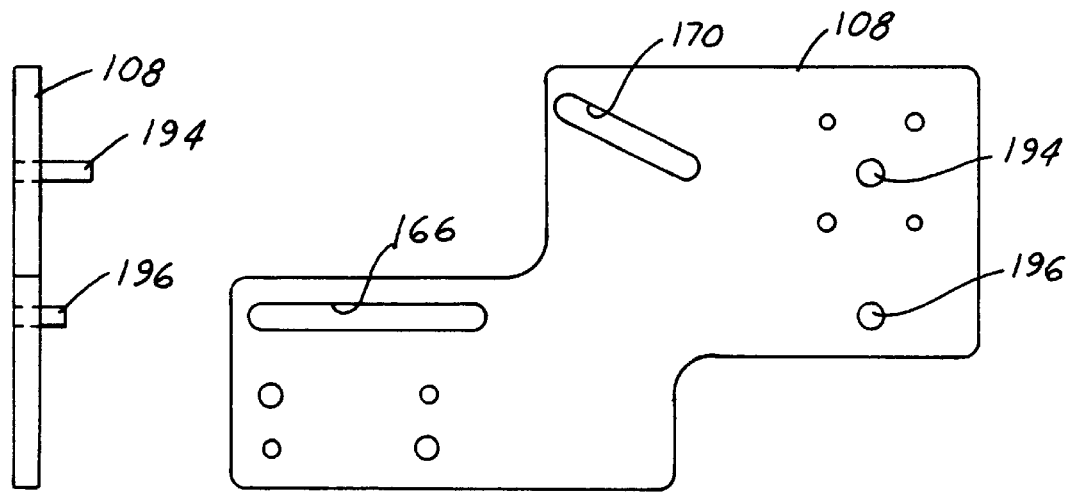
FIG.25　　　　　　FIG.24

CONTAINER FINISH CHECK DETECTION

The present invention is directed to inspection of containers for commercial variations that affect the optical properties of the containers, and more particularly to a method and apparatus for detecting horizontal and vertical checks in the finish of translucent containers.

BACKGROUND AND OBJECTS OF THE INVENTION

In the manufacture of containers such as glass bottles and jars, various types of anomalies can occur in the sidewalls, heels, bottoms, shoulders, necks and finishes of the containers. These anomalies, termed "commercial variations" in the art, can affect commercial acceptability of the containers. It has been proposed to employ electro-optical inspection techniques for detecting commercial variations that affect the optical properties of the containers. The basic principle is that a light source is positioned to direct light energy onto a container, and a camera is positioned to receive light energy after interaction with the portion(s) of the container illuminated by the light source. Commercial variations in the portion of the container illuminated by the light source are detected as a function of the intensity of the light energy incident on the sensor. Detection of commercial variations in a container can result in rejection of the container, depending upon the type of variation. For example, checks, which are mirror-like cracks in a container sidewall or finish, can result in stress concentration and failure of a container, and thus would normally automatically result in container rejection regardless of size or position. On the other hand, blisters in a container finish can be acceptable if sufficiently small in size.

In the art of container manufacture, the term "container finish" generally refers to that portion of the container that defines the container mouth. In a bottle, for example, the finish includes that portion of the container neck having threads and/or beads for receiving the container cap, as well as the upper surface of the neck surrounding the container mouth, termed the "sealing surface," against which the cap seats.

U.S. Pat. No. 4,378,493, assigned to the assignee of the present application, discloses an apparatus and method for inspecting containers, in which glass containers are conveyed in sequence through a plurality of stations where they are physically and optically inspected. Differing mechanical and electro-optical inspections are performed at the sequential stations, typically one inspection per station. The number of inspections that can be performed is thus limited by the number of stations in the apparatus.

U.S. Pat. No. 5,200,801, also assigned to the assignee of the present application, discloses a method and apparatus that can be implemented at one of the inspection stations for detecting vertical checks in the finish of a translucent container. A light source directs light energy onto the container finish from externally of the container finish laterally of the container axis over an angular portion less than the entire circumference of the container finish. An area array camera is positioned externally of the container at an angle to the container axis to receive an image of the illuminated portion of the container finish. The camera is oriented with respect to the light source such that a vertical check in the container finish reflects light energy from the source to the camera to create a bright image of the check against a normally dark background. Vertical checks in the container finish are detected as a function of such reflected light energy. Use of an area array sensor permits detection of vertical checks over an increased angular range with respect to the radius of the container finish.

It is a general object of the present invention to provide an apparatus and method for detecting checks in the finish of a translucent container in which a container finish may be inspected for both horizontal and vertical checks at a single inspection station, thus improving efficiency of the inspection process. Another object of the present invention is to provide a method and apparatus of the described character that are user friendly, and that can be readily adjusted in the field for inspecting container finishes of differing diameter. Yet another object of the present invention is to provide a method and apparatus of the described character that detect both horizontal and vertical checks over an increased angular range as compared with the prior art. A further object of the invention is to provide a method and apparatus of the described character for detecting checks in the finish of a translucent container that provide improved uniformity of illumination at the container finish inspection area, and that eliminate spherical aberration in the illumination beams.

SUMMARY OF THE INVENTION

Apparatus for detecting checks in the finish of a translucent container in accordance with one aspect of a presently preferred embodiment of the invention includes a first light source for directing first light energy onto a first portion of the container finish as it is rotated about its axis, and a second light source for directing second light energy onto a second portion of the container finish as it rotates. A first light sensor is disposed with respect to the first light source and the container finish to receive portions of the first light energy reflected from horizontal checks in the container finish. A second light sensor is disposed with respect to the second light source and the container finish to receive portions of the second light energy reflected from vertical checks in the container finish. An information processor is coupled to the first and second sensors for detecting horizontal and vertical checks in the container finish as a function of reflected portions of the first and second light energies. In the preferred embodiment of the invention, the first and second sensors comprise linear array sensors that are scanned at increments of container rotation. The information processor detects not only presence of reflections from the container finish as a function of position of incidence on the linear array sensor, but also angular position of the reflections as a function of container rotation. The information processor may distinguish check variations at the container finish, at which light from the first light source is reflected onto the first sensor or light from the second light source is reflected onto the second sensor, from blister variations at the container finish at which light from both the first and second sources is reflected onto the associated sensors. In this way, containers with horizontal or vertical check variations can be rejected, while containers with blister variations can be analyzed and rejected only if blister size exceeds a preset threshold.

In the preferred embodiment of the disclosed invention, the first light source and sensor for detecting horizontal checks are disposed in a vertical plane, preferably coplanar with the container axis of rotation, and a third light source and sensor are provided at mirror-image position with respect to the second light source and sensor on opposed sides of the vertical plane. In this way, vertical checks are detected over an increased angular range with respect to the radius of the container finish. The light sources and sensors preferably include fresnel lenses for further increasing the angles of check detection and to eliminate spherical aberrations. The linear array light sensors are mounted with associated lenses at an angle to the container finish in a scheimpflug arrangement with respect to the associated viewed area on the container finish, so that the sensor is in focus from the top to the bottom of the associated viewed area. The several light sources preferably are coupled by fiber optic cables to a common halogen light box that includes internal regulation so as to provide constant illumination in spite of power variations, aging of the halogen bulb and intensity variations among bulbs, for example. The fiber optic bundle ends at each light source are oriented to illuminate a rectangular area of the container finish, which accommodates wobble and other inconsistencies in container handling.

The first light source and sensor for detecting horizontal checks in the preferred embodiment of the invention are disposed above the horizontal plane of the container mouth, and in a vertical plane that preferably is coplanar with the container axis of rotation. The second and third light sources are positioned on opposite sides of this vertical plane, and beneath the horizontal plane of the container mouth, at equal but opposite angles with respect to the container axis. Likewise, the second and third light sensors are disposed above the horizontal plane of the container mouth and on opposite sides of the vertical plane. The first light source illuminates an interior surface of the container finish through the container mouth, and the first camera views the opposing external surface of the container finish. The second and third light sources illuminate respective exterior areas of the container finish on opposite sides of the area illuminated by the first light source, and the second and third light sensors view the associated areas of illumination at the inside surface of the container finish through the container mouth. In the preferred embodiment of the invention, and in accordance with another aspect of the invention, the first light source and sensor, the second light source and sensor, and the third light source and sensor are mounted in associated optical subassemblies, each of which includes a flat mounting plate. These plates are mounted in assembly in sliding relationship with relation to each other, and the plates have interlocking grooves and pins so that all three optical subassemblies are simultaneously adjustable with respect to each other to accommodate containers of differing finish diameters.

A method of detecting checks in the finish of a translucent container in accordance with yet another aspect of the present invention includes the steps of rotating the container about its central axis while simultaneously directing first and second light energies onto differing portions of the container finish. First and second light sensors are positioned to receive portions of the first and second light energies reflected from checks in the container finish. The first and second light sensors are oriented with respect to the associated light sources and the container finish for receiving portions of the associated light energies reflected from horizontal and vertical checks in the container finish respectively. Horizontal and vertical checks in the container finish are detected as a function of the reflected portions of the first and second light energies. Horizontal checks at the container finish, which reflect light from the first light source onto the first sensor, are distinguished from vertical checks in the container finish that reflect light from the second source onto the second sensor, and from bubbles in the container finish from which light is reflected from both light sources onto both associated sensors.

BRIEF DESCRIPTION OF THE DRAWINGS

The invention, together with additional objects, features and advantages thereof, will be best understood from the following description, the appended claims and the accompanying drawings in which:

FIG. 4 is a perspective schematic diagram of the optics in FIGS. 1 and 2 for detecting horizontal checks in the container finish;

FIG. 5 is a perspective view of a container finish that illustrates areas of illumination of the respective light sources and fields of view of the respective sensors in FIGS. 1–4;

FIG. 6 is a schematic diagram of a scheimplug optical arrangement employed at each light sensor in FIGS. 1–4;

FIGS. 22 and 23 are respective top plan and side elevational views of one of the vertical check subassembly mounting plates;

FIGS. 24 and 25 are respective top plan and side elevational views of the other vertical check subassembly mounting plate;

DETAILED DESCRIPTION OF PREFERRED EMBODIMENTS

Figure 1:
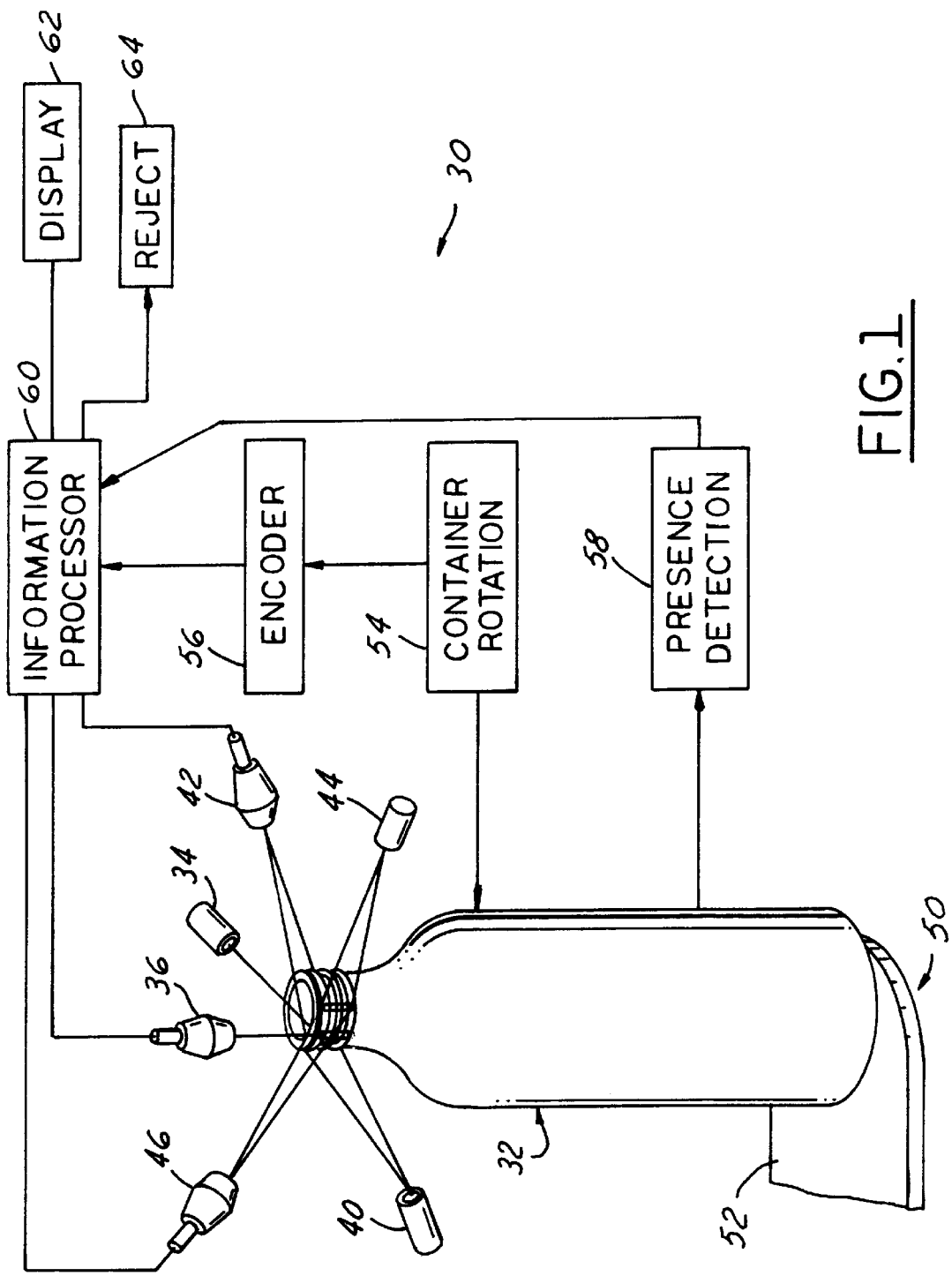
FIG. 1 is a schematic diagram of apparatus for detecting checks in the finish of a translucent container in accordance with a presently preferred embodiment of the invention.
Figure 2:
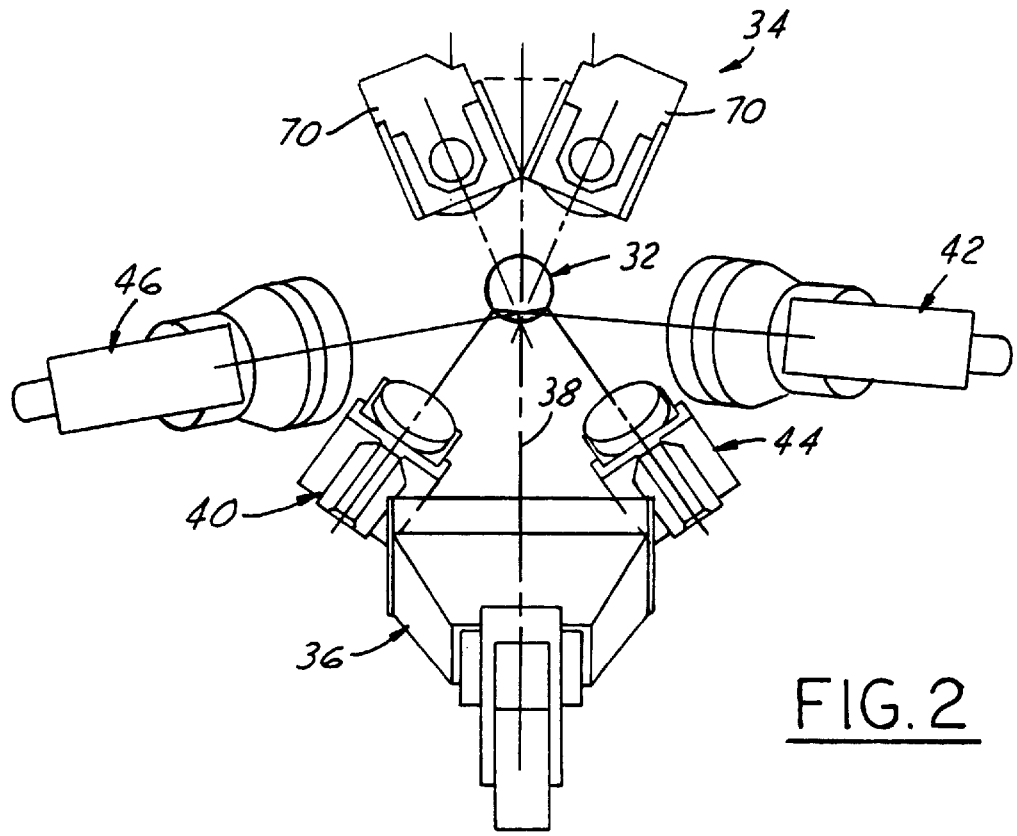
FIG. 2 is a top plan view of the inspection optics illustrated schematically in FIG. 1.
Figure 3:
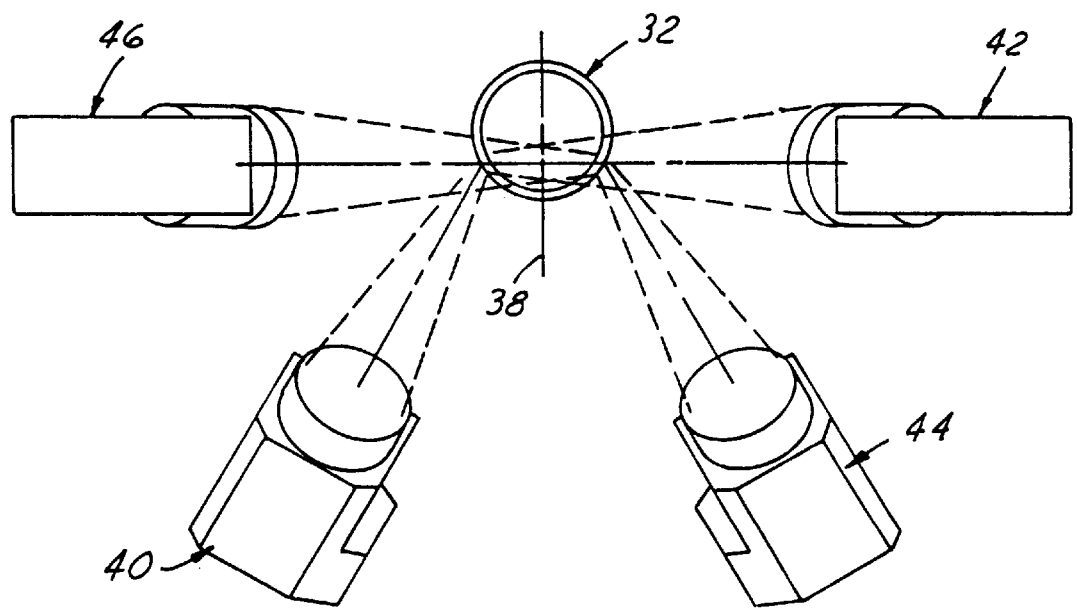
FIG. 3 is a top plan view of the portion of the inspection optics in FIGS. 1 and 2 for detecting vertical checks in a container finish.
Figure 9:
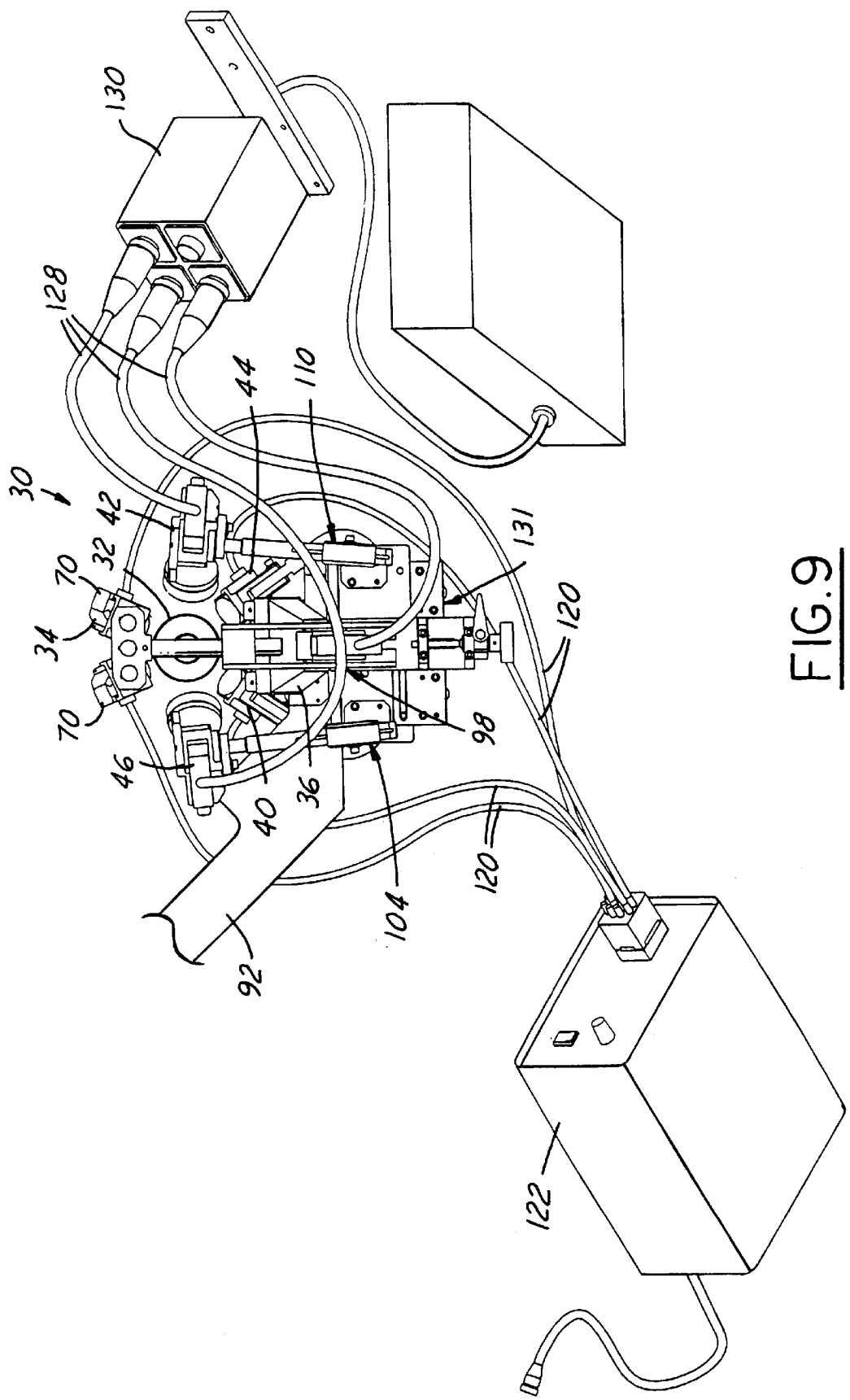
FIG. 9 is a fragmentary perspective view of the apparatus for detecting checks in a translucent container finish in accordance with the presently preferred embodiment of the invention.
Figure 10:
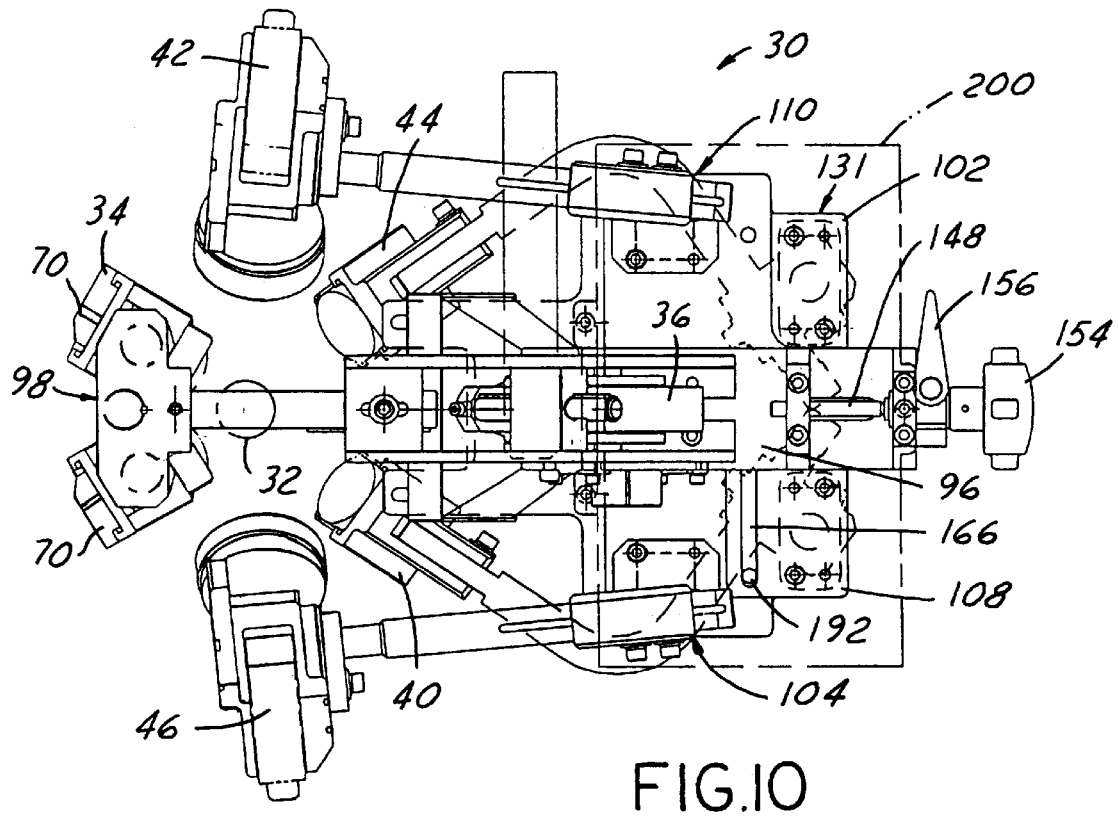
FIG. 10 is a top plan view of the inspection optics in FIG. 9.
Figure 11:
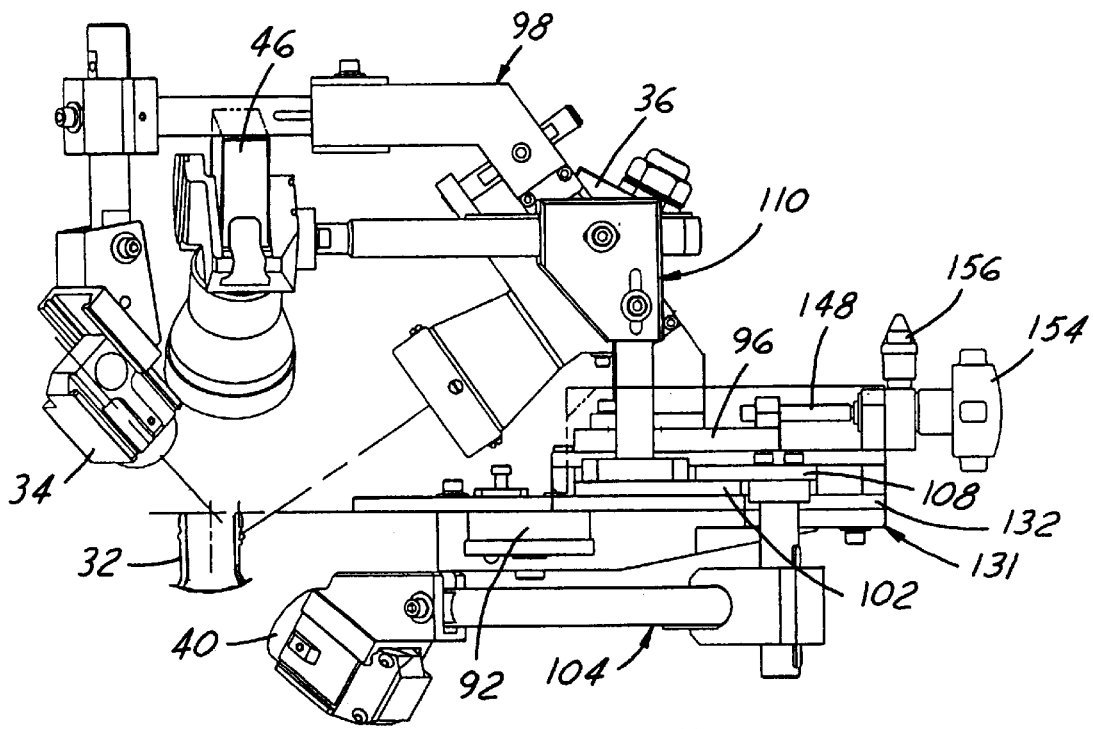
FIG. 11 is a side elevational view of the inspection optics in FIGS. 9 and 10.
Figure 12:
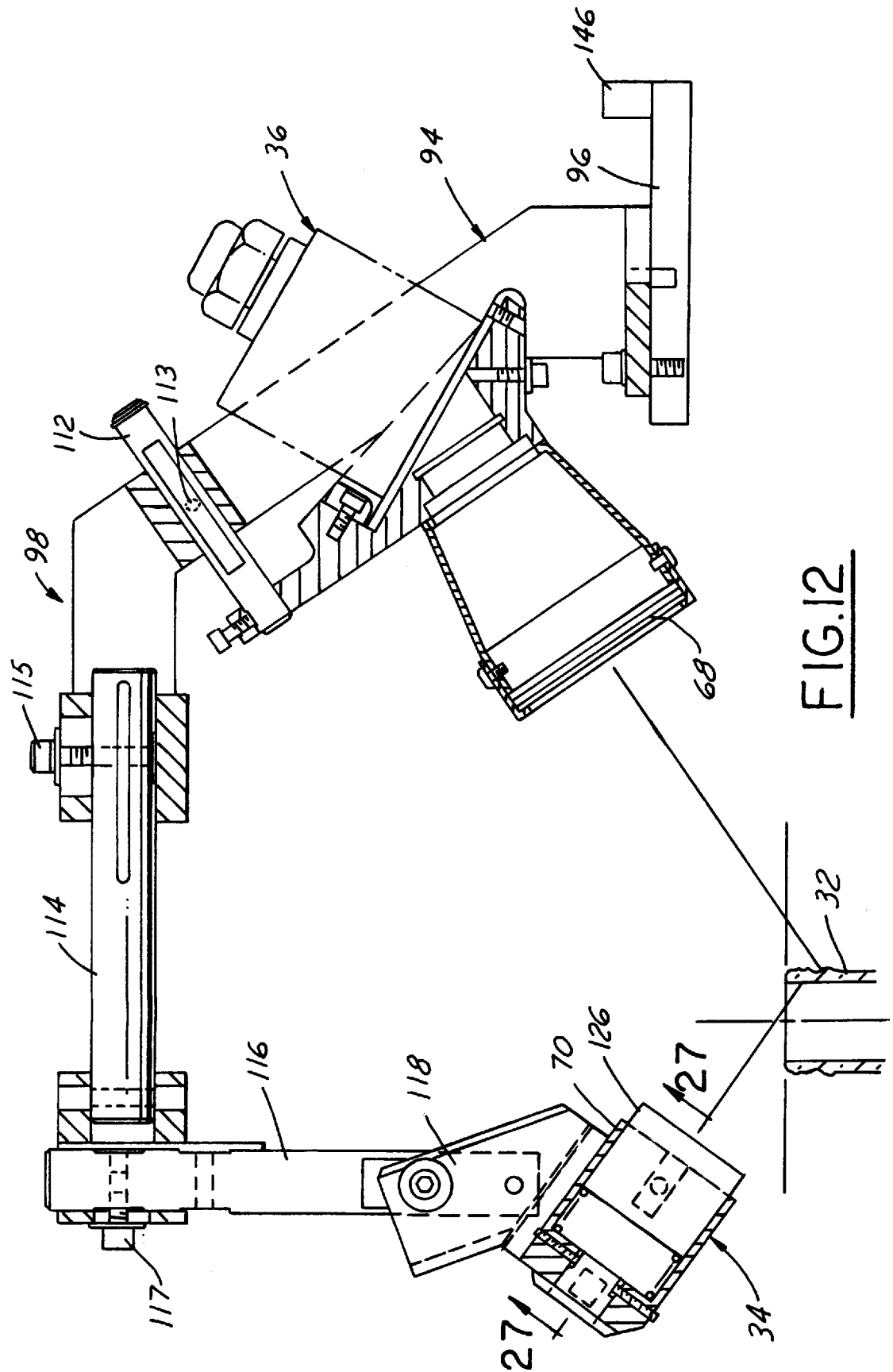
FIG. 12 is a partially sectioned side elevational view of a portion of the inspection optics for detecting horizontal checks in the container finish.

FIGS. 1–4 schematically illustrate an apparatus 30 for detecting horizontal and vertical checks in the finish of a container 32 in accordance with a presently preferred embodiment of the invention. A first light source 34 is positioned to direct a first beam of light energy downwardly at an angle through the container mouth onto an opposing inside surface of the container finish. A first light sensor 36 is disposed on the opposite side of the container finish from light source 34, and views the external surface of the container finish in the area opposite to the internal area of illumination from light source 34. As best seen in FIG. 2 (and FIGS. 9–12), light source 34 and light sensor 36 are disposed in a vertical plane 38 that is preferably coplanar with the axis of rotation of container 32. A second light source 40 is positioned beneath the horizontal plane of the mouth of container 32 (and beneath the sensor 36), and is directed upwardly at an angle to illuminate an exterior portion of the container finish. A second light sensor 42 is disposed on the opposite side of the container (i.e., on the opposite side of vertical plane 38), and is directed downwardly at an angle through the container mouth to view the interior surface of the container finish in an area opposite to the area of illumination from light source 40. Likewise, a third light source 44 is disposed beneath the horizontal plane of the container mouth (and beneath sensor 36), and is angulated upwardly to direct an associated light beam onto a third portion of the container finish exterior. An associated third light sensor 46 is positioned to view the inside surface of the container finish, through the container mouth, in an area opposite to the area of exterior illumination from light source 44. As best seen in FIGS. 2–3 (and FIGS. 9–11), the mounting arrangements for light source/sensor pairs 40, 42 and 44, 46 are mirror images of each other.

A conveyor 50 (FIG. 1), typically including a starwheel (not shown) and a slide plate 52, is so disposed and connected to a source of molded containers as to bring successive containers 32 into position at the inspection station defined by apparatus 30. Conveyor 50 may be of any suitable type, such as those shown in U.S. Pat. Nos. 4,230,219 and 4,378,493, and would typically include a rotatable starwheel for bringing successive containers into position and holding the containers in fixed position during the scanning operation. A container rotating device 54, such as a drive roller, is positioned to engage container 32 at station 30, and to rotate the container about its central axis. An encoder 56 is coupled to the container rotation mechanism to provide signals indicative of increments of container rotation. Alternatively, the container may be rotated at constant velocity and increments of container rotation determined at equal time increments. A detector 58, such as an optical switch, is positioned to provide a signal indicative of presence of container 32 at station 30. An information processor 60 is coupled to encoder 56, detector 58 and sensors 36, 42, 46 for detecting vertical checks and other commercial variations in the container finish, as will be described. Information processor 60 is also coupled to a display 62 for providing an alphanumeric and/or graphic display of container inspection information to an operator, and to a reject mechanism 64 for removing from the conveyor system containers that do not pass inspection.

Each light source 34, 40, 44 illuminates an associated substantially rectangular portion 34a, 40a, 44a of the container finish, as best seen in FIG. 5. As noted above, the illumination beam from light sources 40, 44 are incident on the exterior surface of the container finish, while the illumination beam from light source 34 is incident on the interior surface of the container finish through the container mouth. Each area of illumination 34a, 40a, 44a is of rectangular geometry, having a long dimension extending in the axial direction from just below the container take-out bead substantially to the sealing surface at the upper edge of the container mouth. Thus, the entire axial portion of the container finish is illuminated by each beam, and the entire circumference of the container finish is swept by each beam as the container is rotated. Each light sensor 36, 42, 46 comprises a linear array sensor 66 (FIG. 6) coplanar with the container axis of rotation—i.e., an array of picture elements or pixels disposed in a linear array, consisting of 512 pixel elements in the preferred embodiment of the invention. Each linear array sensor 66 of each sensor 36, 42, 46 is mounted in association with a lens 68 in a so-called scheimpflug arrangement illustrated in FIG. 6 so that each linear array sensor 66 is focused over the entire opposing image area of the container finish. Sensor 36 has an image area 36a (FIG. 5) disposed within the area 34a of illumination from light source 34. Likewise, the linear arrays of sensors 42, 46 have image areas 42a, 46a within the areas 40a, 44a of illumination from associated light sources 40, 44. The image areas of sensors 36, 42, 44 preferably extend over the entire axial length of the container finish from just below the take-out bead to the upper edge or sealing surface of the container mouth, and are nominally centrally positioned within the area of illumination of the associated light source. The use of rectangular illumination beams accommodates mishandling, wobble and tolerance variations in the containers.

As noted above, light source 34 illuminates area 34a at the interior surface of the container finish through the container mouth. A portion of the exterior surface of the container finish is imaged onto sensor 36. As best seen in FIG. 3, light sources 40, 44 illuminate the exterior surface of the container finish, while sensors 42, 46 are imaged onto the opposing interior surface portions of the container finish through the container mouth. In the embodiment of the invention illustrated in the drawings, light source 34 comprises a pair of adjacent illumination lens assemblies 70. The use of two lens assemblies 70 disposed adjacent to and at an angle with respect to each other (FIG. 2) increases the angle of illumination from light source 34 at the container finish, and thus increases the angular range of detection of horizontal checks. Alternatively, light source 34 can comprise a single lens assembly with an associated wide angle fresnel lens for increasing the angle of illumination rays. All light sources and sensors preferably include fresnel lenses cost effectively to increase angular range and greatly to reduce spherical aberrations in the illumination beams. In one embodiment of the present invention, light source 34 and associated sensor 36 are disposed in opposition to each other in the plane 38 of the container axis of rotation as previously described, and are oriented downwardly at an angle of 45° with respect to the container axis (see FIGS. 11 and 12). Light sources 40, 44 are positioned beneath the horizontal plane of the container mouth (see FIG. 11), are directed upwardly at an angle of 45° with the container axis, and are spaced by an angle of 35° on opposite sides of vertical plane 38. Light sensors 42, 46 are disposed above the horizontal plane of the container mouth at an angle of 45° to the container axis (see FIG. 11), and are spaced 170° from each other—i.e., each 85° from vertical plane 38. Light sources 40, 44 are biased or offset by 20°—i.e., a 40° camera angle minus 20° bias angle, thus equaling an incidence angle of 20°.

Figure 7A:
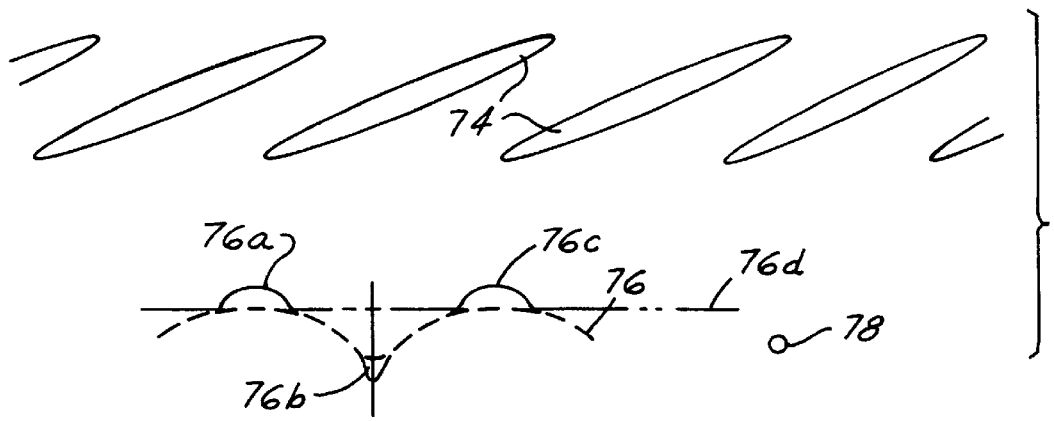
FIGS. 7A, 7B and 7C are graphic illustrations useful in describing operation of the invention.
Figure 7B:
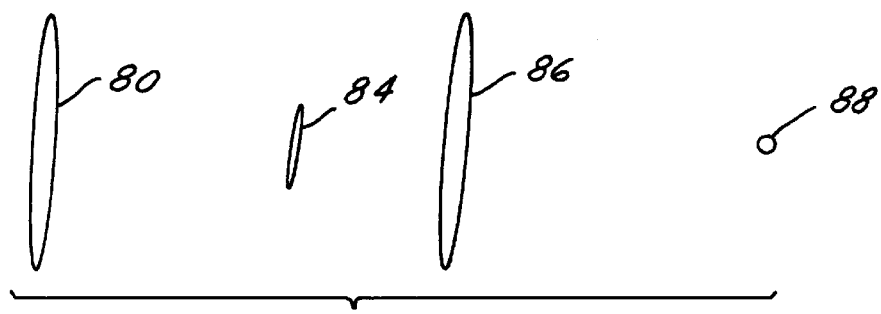
Figure 7C:

In operation, light source 34 and light sensor 36 cooperate with each other to detect horizontal checks in the container finish, while light source/sensor pairs 40, 42 and 44, 46 function to detect vertical checks in the container finish. Referring to FIGS. 7A–7C, FIG. 7A illustrates an exemplary output from horizontal check sensor 36, while FIGS. 7B and 7C illustrate exemplary outputs from vertical check sensors 42, 46 respectively. In each FIG. 7A–7C, the horizontal dimension is in scan increments around the container and the vertical dimension is in pixels in the associated light sensor. Each sensor 36, 42, 46 provides a normally dark-field output to information processor 60, against which reflections from checks appear as bright spots or areas. Image processor 60 scans the various sensors at increments of container rotation. These scans are effectively laid down next to each other in computer memory to provide unwrapped images of the container finish. FIGS. 7A–7C provide unwrapped schematic illustrations of the respective sensor outputs. The angular offsets between the respective sensors is programmed into information processor 60 so that the information processor can align the unwrapped images according to angular position. It will be appreciated that, whereas information processor 60 is illustrated in FIG. 1 as a single element, the information processor may comprise numerous elements, including information preprocessing on the sensors themselves or in the associated sensor housings.

Figure 8:
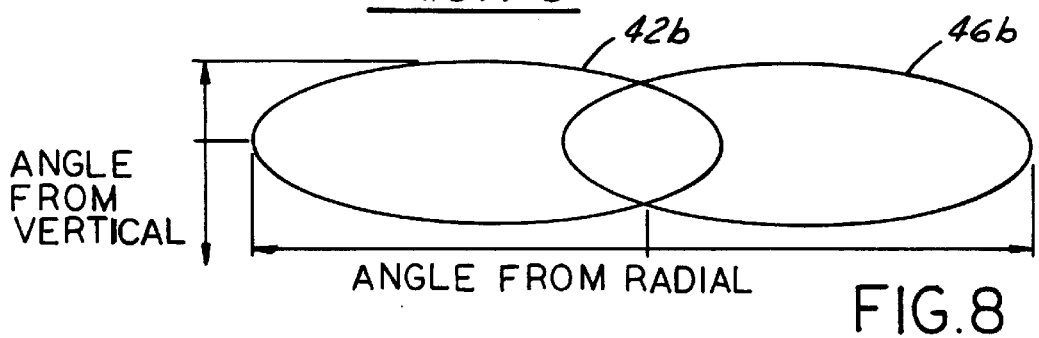
FIG. 8 is a graphic illustration useful in describing detection of vertical checks in accordance with the preferred embodiment of the invention.

FIG. 7A illustrates an exemplary output from horizontal check sensor 36, including reflections 74 indicative of the threads on the container finish. A horizontal check 76 in the container finish may be either flat or wavy, and provides a bright output 76a, 76b, 76c in each area at which check 76 approaches horizontal orientation. As noted above, the use of dual lens assemblies 70 with associated fresnel lenses increases the angle of detection of horizontal checks as compared with true horizontal 76d. A small spot reflection 78 is also illustrated in FIG. 7A. FIG. 7B illustrates an exemplary output of first vertical check sensor 42, while FIG. 7C illustrates an exemplary output of second vertical check sensor 46. A reflection 80 at sensor 42 (FIG. 7B) and a concurrent reflection 82 at sensor 46 (FIG. 7C) may indicate a large vertical check at an angle close to radial, or a split seam in the container resulting from the molding operation. Referring to FIG. 8, sensor 42 is angled to receive reflections from vertical checks over a range of angles 42b in one direction from radial orientation, while sensor 46 is oriented to detect reflections from vertical checks at a range 46b of angles in the opposite direction from radial. These angular ranges 42b, 46b overlap with each other near radial orientation, so that detection of a reflection at both sensors at a given angular position of the container may illustrate a vertical check or other reflective variation at or near radial orientation, while detection of a reflection at one but not both sensors may indicate a vertical check or other reflective variation at a greater angle from radial. Sensors 42, 46 also detect reflections from vertical checks at other than vertical orientation over the range of angles illustrated in FIG. 8.

Returning to FIGS. 7B and 7C, sensor 42 receives a reflection 84 at an angular position for which no corresponding reflection is received at sensor 46 (FIG. 7C), thus indicating a vertical check at an angular orientation within the range of sensor 42 but not within the range of sensor 46. The reflection 86 at sensor 42 (FIG. 7B) but not sensor 46 (FIG. 7C) may indicate a large vertical check, or an offset seam in the container finish. If, for example, reflections 80 and 86 are 180° apart, then reflections 80 and 82 (FIGS. 7A and 7B) would be interpreted as indicating a split seam, while reflection 86 would be interpreted as indicating an opposing offset seam. Spot reflection 88 at sensor 42 (FIG. 7B) and spot reflection 90 at sensor 46 (FIG. 7C), at the same angular position as spot reflection 78 at sensor 36 (FIG. 7A), indicates presence of a bubble at this angular position. Presence of a bubble may or may not necessitate rejection of the container depending upon size. Thus, detection of a horizontal check 76, a split seam 80, 82 or a vertical check 84 would normally result in rejection of the container, while detection of a bubble by reflections 78, 88, 90 at all three sensors may or may not cause rejection of the container depending upon comparison of bubble size with a threshold size set by an operator. Detection of an offset seam 86 may or may not call for rejection of the container, again depending upon parameters set by an operator. Areas of occurrence of expected features, such as the container threads and the container take-out bead, can be programmed into the information processor, so that the information processor can ignore or inhibit rejection of containers when these features are detected at their expected positions.

Figure 13:
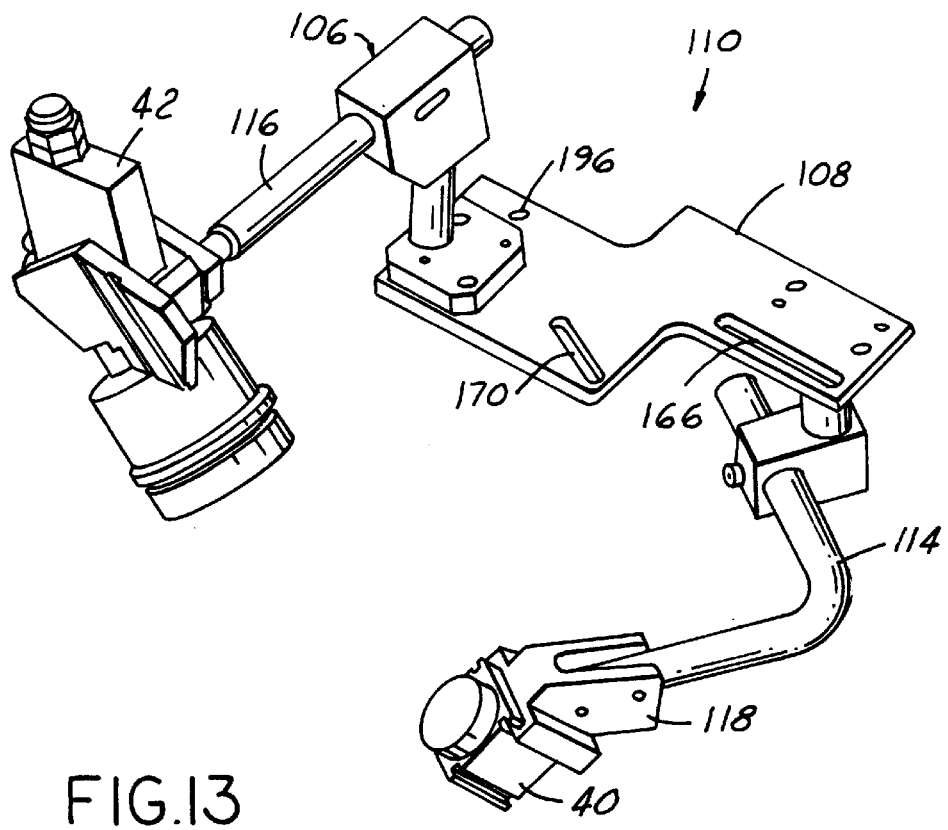
FIGS. 13 and 14 are perspective views of portions of the inspection optics for detecting vertical checks in the container finish.
Figure 14:
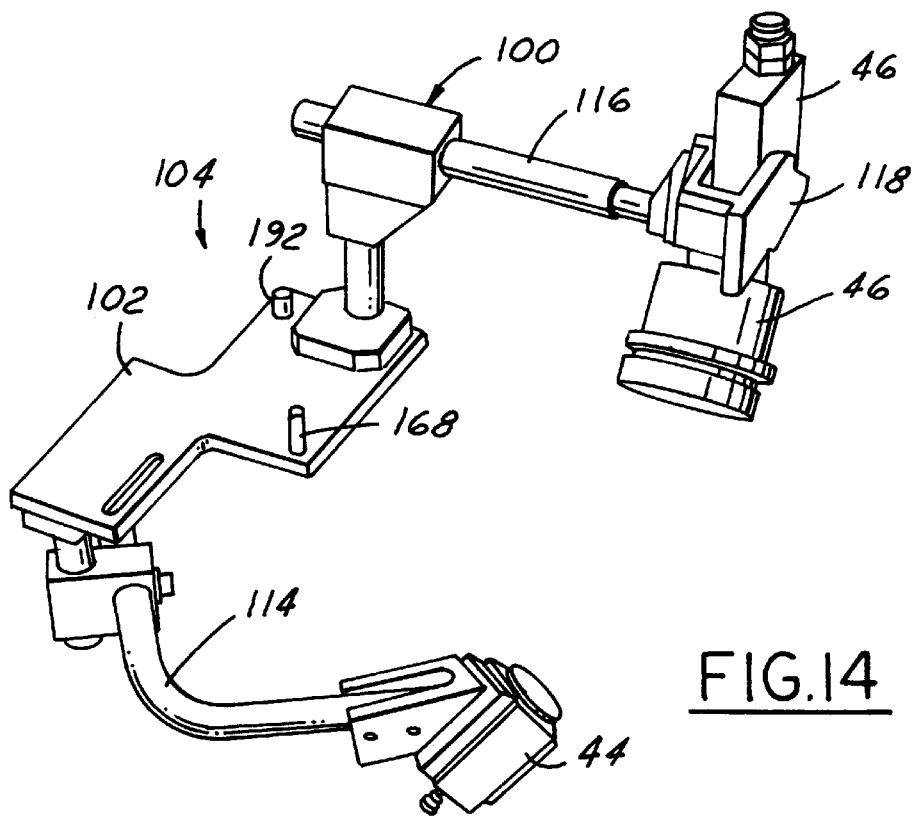
Figure 15:
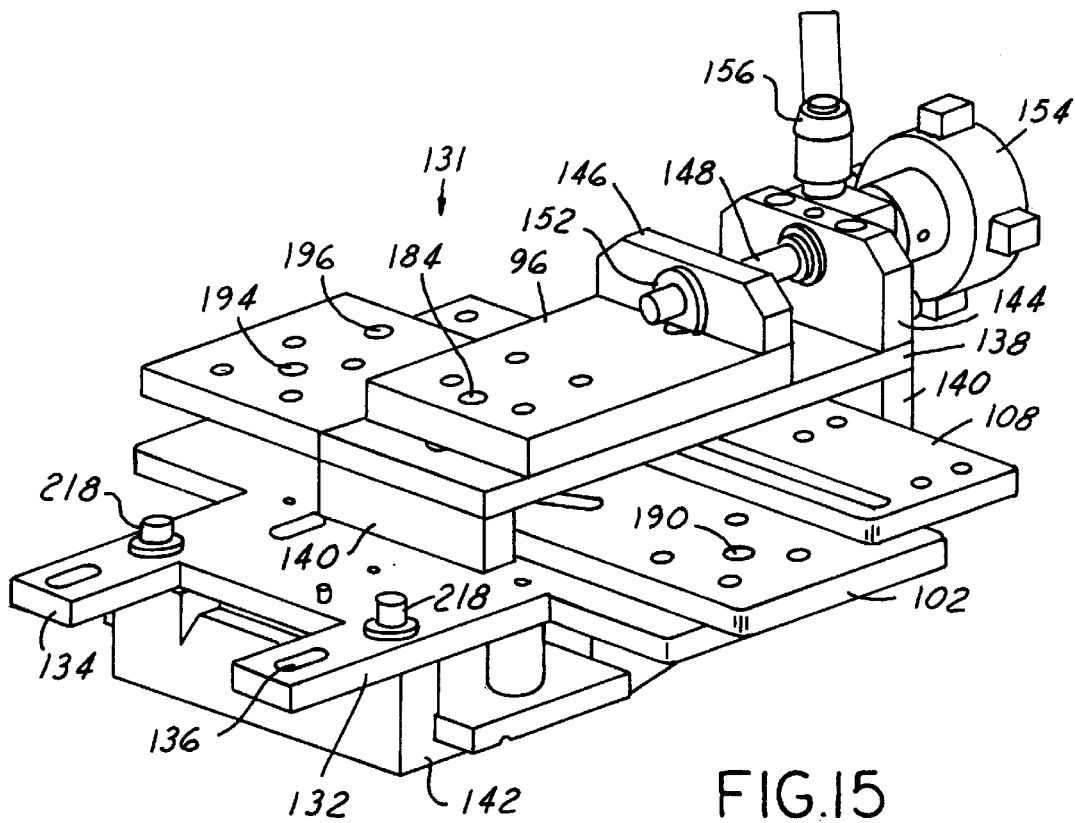
FIG. 15 is a perspective view of the optical subassembly mounting base in accordance with the present invention, with inspection optics removed for purposes of clarity.
Figure 17:
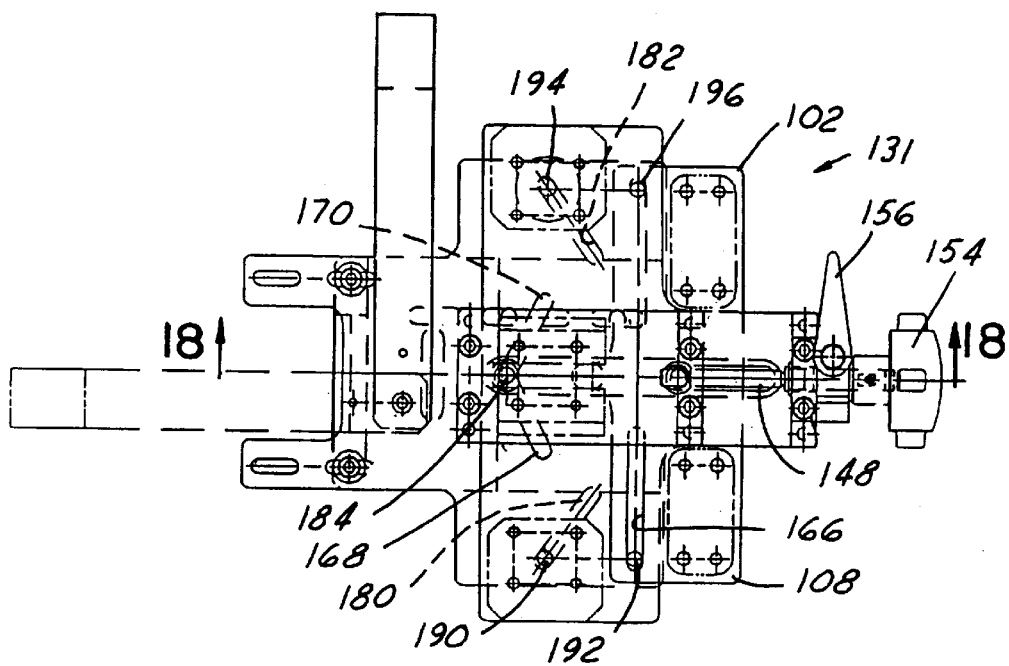
FIG. 17 is a top plan view of the inspection optics mounting base in FIGS. 15–16.
Figure 16:
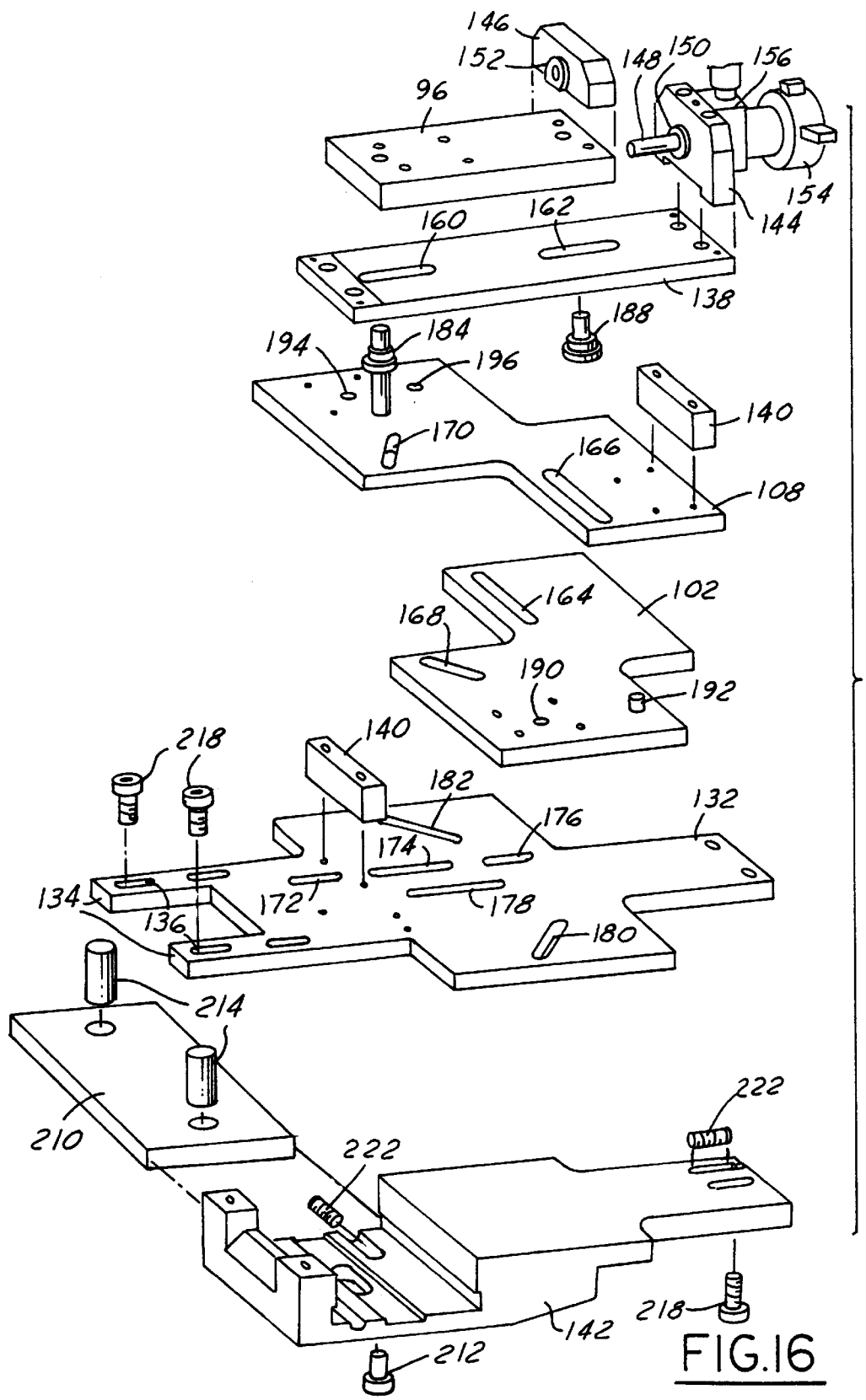
FIG. 16 is an exploded perspective view of the inspection optics mounting base illustrated in FIG. 15.
Figure 18:
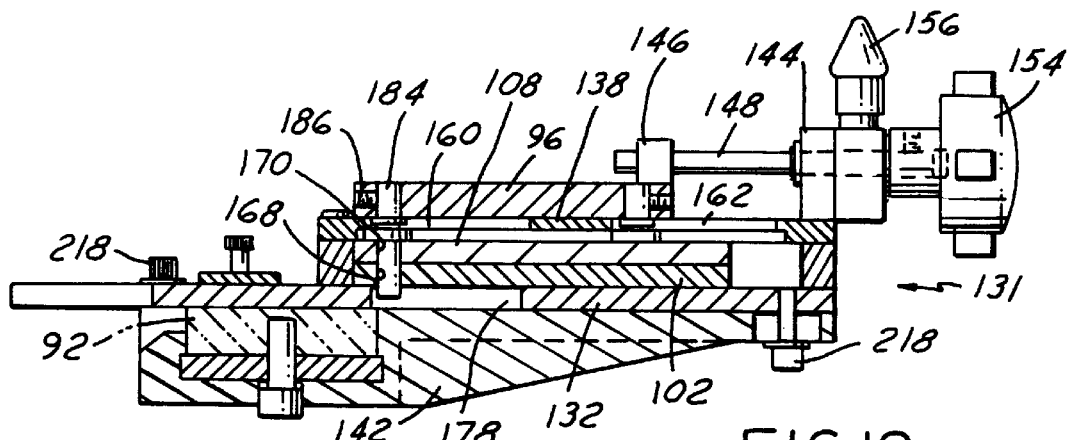
FIG. 18 is a sectional view taken substantially along the line 18—18 in FIG. 17.
Figure 19:
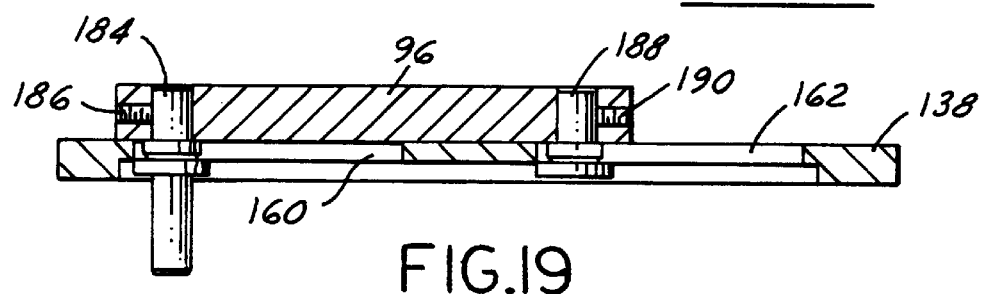
FIG. 19 is a sectional view on an enlarged scale of a portion of the mounting base illustrated in FIG. 18.

FIGS. 9–27 illustrate physical construction of apparatus 30 in accordance with a presently preferred embodiment of the invention. Apparatus 30 is provided as an assembly for mounting by an operator on the headplate 92 of an inspection machine, preferably of the type disclosed in above-noted U.S. Pat. Nos. 4,230,219 and 4,378,493. As shown in FIG. 1, headplate 92 is positioned at the level of the sealing surface that surrounds the mouth of the containers 32 to be inspected. First light source 34, comprising lens assemblies 70 and first light sensor 36, are mounted by associated bracketry 94 (FIG. 12) to an associated mounting slide plate 96 to form a first optical subassembly 98. Second light source 44 and associated second sensor 46 are mounted by associated bracketry 100 (FIG. 14) to a mounting plate 102 to form a second optical subassembly 104. Likewise, third light source 40 and associated third sensor 42 are mounted by associated bracketry 106 (FIG. 13) to a third mounting plate 108 to form a third optical subassembly 110. The mounting bracketry of each optical subassembly includes an adjustment rod 112 (FIGS. 12–14) and associated setscrews 113 for adjusting focus of the associated sensor and fresnel lens. Likewise, the mounting bracketry of each optical subassembly includes slidable rods 114, 116 and associated setscrews 115, 117 for adjusting position of light source lens assemblies 70, and bracketry 118 for adjusting lens assembly angular orientation. Each light source comprises one or more lens assemblies 70 connected by fiber optic cabling 120 (FIGS. 9 and 27) to a common source of light energy 122. All optical subassemblies 98, 104, 110 are preferably adjusted at the factory to place the light sources and sensors at proper orientation and position with respect to each other, and should not require further internal adjustment in the field in the absence of disassembly for repair. In the currently preferred embodiment of the invention, common light source 122 comprises a halogen light source with internal programming and feedback to maintain a constant intensity of illumination unaffected by line voltage, bulb age or intensity variance between bulbs. Common light source 122 also includes facility for extinguishing the halogen bulb in the event of termination of operation at the inspection apparatus. Common light source 122 may also include facility for rapid adjustment of light intensity for translucent glass containers of differing opacity—e.g., flint and amber glass. Thus, all light sources 34, 40, 44 illuminate the container finish simultaneously as the container rotates. At each lens assembly 70, a mirror 124 (FIG. 27) is disposed at an angle to fiber optic bundle 120 for reflecting the light energy emerging from the fiber optic bundle through a fresnel lens 126 onto the associated illumination area of the container. As noted above, the illumination areas are of rectangular geometry, with long dimensions oriented axially of the container finish. The fiber optic bundles are randomized to provide uniform illumination across all optical bundles. All light sensors 36, 42, 46 are connected by associated electrical cabling 128 (FIG. 9) through a junction box 130 to information processor 60.

In accordance with one aspect of the present invention summarized above, the optical subassemblies of the present invention are mounted to each other in such a way that the assemblies are simultaneously adjustable with respect to each other for accommodating differing container finish diameters. The adjustable base assembly 131 for implementing this feature of the invention is illustrated in FIGS. 15–24 with bracketry and optics removed to facilitate understanding. Referring to these drawings figures, a flat bottom plate 132 has a pair of spaced legs 134 with slotted openings 136 for mounting base assembly 131 on headplate 92 (FIGS. 9, 15 and 17) of the inspection system. A flat bridge plate 138 is fixedly secured parallel to bottom plate 132, being spaced therefrom by a pair of spacers 140. Mounting plates 102, 108 of vertical check optical subassemblies 104, 110 (FIGS. 13—14) are slidably mounted between bottom plate 132 and bridge plate 138 in sliding facing engagement with each other, and in sliding facing engagement with bottom plate 132. Slide plate 96 of horizontal check optical subassembly 98 (FIG. 12) is slidably carried on bridge plate 138. A clamp mounting plate 142 is secured to the bottom face of bottom plate 132 to secure apparatus 30 to headplate 92. A bearing plate 144 is secured at one end of bridge plate 138, and an adjustment plate 146 is secured at one end of slide plate 96. A leadscrew 148 rotatably extends through a bearing 150 in bearing plate 144, and is rotatably coupled to a nut 152 on adjustment plate 146. A knob 154 is mounted on the opposing end of leadscrew 148, and a lock mechanism 156 is secured on bearing plate 144 for selectively locking leadscrew 148 in position.

Bridge plate 138 has a pair of longitudinally spaced aligned slots 160, 162. (Directional adjective such as "longitudinal" and "lateral" in connection with description of mounting base assembly 131 are taken with respect to vertical plane 38 of horizontal check detector optical subassembly 98.) Each optical subassembly mounting plate 102, 108 includes an associated laterally oriented slot 164, 166, and an associated angularly oriented slot 168, 170. Bottom plate 132 has three longitudinally oriented aligned slots 172, 174, 176, a fourth longitudinally oriented slot 178 spaced laterally from slot 174, and a pair of angulated slots 180, 182 respectively parallel to slots 170, 168 in plates 108, 102. A pin 184 is secured to horizontal check subassembly slide plate 96 by a setscrew 186 (FIGS. 18 and 19), and extends downwardly through slot 160 in bridge plate 138, and through angulated slots 170, 168 in vertical check mounting plates 108, 102 into longitudinal slot 178 in bottom plate 132. A second pin 188 is secured to horizontal check slide plate 96 by means of a setscrew 190 (FIGS. 18 and 19), and extends into slot 162 of bridge plate 138. Thus, horizontal check slide plate 96 is constrained to move longitudinally with respect to bridge plate 138 by means of pins 184, 188 in slots 160, 162.

First vertical check optical subassembly mounting plate 102 has a first pin 190 (FIGS. 15–17 and 22–23) that extends downwardly in assembly, and is slidably received in angulated slot 180 in bottom plate 132. Plate 102 has a second pin 192 that extends upwardly in assembly, and is slidably received within lateral slot 166 of second vertical check subassembly mounting plate 108. Second vertical check subassembly mounting plate 108 has a first pin 194 (FIGS. 15–17 and 24–25) that extends downwardly in assembly, and is slidably received in angulated slot 182 of bottom plate 132. Plate 108 has a second pin 196 that extends downwardly in assembly and is slidably received within lateral slot 164 of first vertical check optical subassembly mounting plate 102. Thus, horizontal optical subassembly slide plate 96 is constrained by pins 184, 188 and slots 160, 162 to move in the linear direction longitudinally of the inspection station. Vertical check mounting plates 102, 108 are constrained by pins 192, 196 the inspection station. Vertical check mounting plates 102, 108 are constrained by pins 192, 196 and slots 164, 166 to move laterally with respect to each other, and by pins 190, 194 and slots 180, 182 to move at an angle (preferably 55°) with respect to the longitudinal direction.

Figure 26:
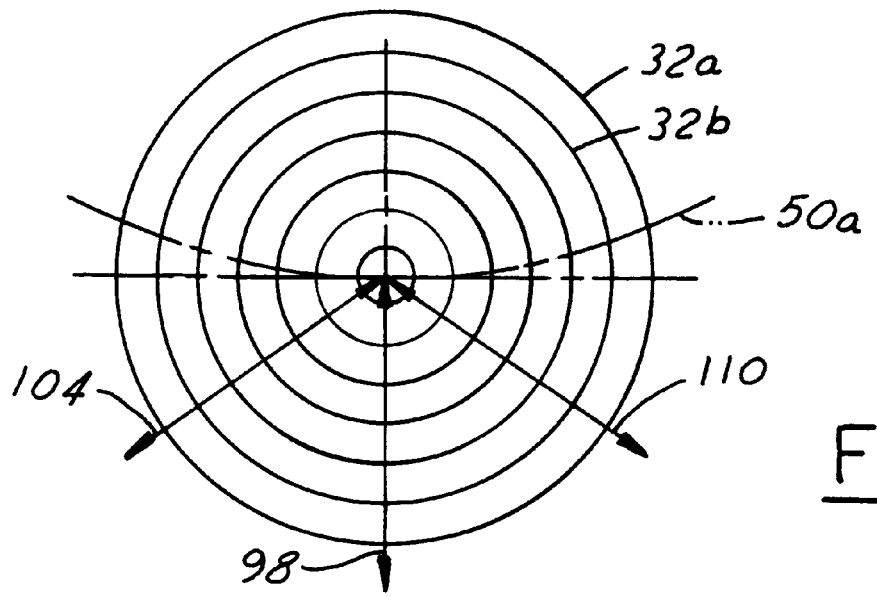
FIG. 26 is a schematic diagram that illustrates simultaneous adjustment of the optical subassemblies in accordance with one aspect of the present invention.
Figure 27:
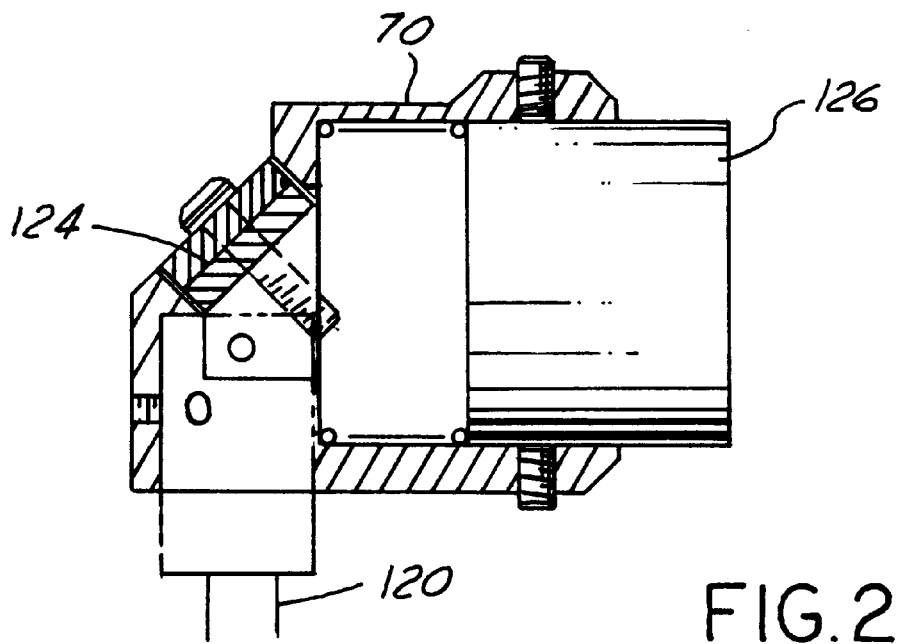
FIG. 27 is a sectional view taken substantially along the line 27—27 in FIG. 12.

Horizontal check slide plate 96 is coupled to knob 154 by leadscrew 148 as previously described, and plate 96 is drivingly coupled to plates 102, 108 by means of pin 184 and angulated slots 168, 170. Thus, as horizontal check slide plate 96 is moved longitudinally inwardly and outwardly by rotation of knob 154, plates 102, 108 are simultaneously moved angularly inwardly and outwardly by means of pin 184 in slots 168, 170. This simultaneous adjustment feature is illustrated in FIG. 26. Line 50*a* illustrates the path of movement of containers through the inspection station under control of the conveyor starwheel. The circles 32*a*, 32*b*, . . . illustrate differing finish diameters. Rotation of knob 154 (FIGS. 9–11 and 15–18) simultaneously adjusts horizontal check optical subassembly 98, first vertical check optical subassembly 104 and second vertical check optical subassembly 110 in the directions of the associated lines in FIG. 26 radially inwardly and outwardly with respect to the container axis. Thus, the three subassemblies are simultaneously adjusted by rotation of knob 154 to accommodate container finishes of differing diameters. In the preferred embodiment of the invention, a scale is provided on the housing 200 (FIG. 10) that encloses the base assembly for relating adjusted position to differing finish diameters. When the position of the desired finish diameter is reached, lock 156 is engaged to hold leadscrew 148, and thus the adjusted positions of the optical subassemblies, in fixed position. Knob 154 preferably includes a clutch mechanism to prevent over-turning.

Figure 20:
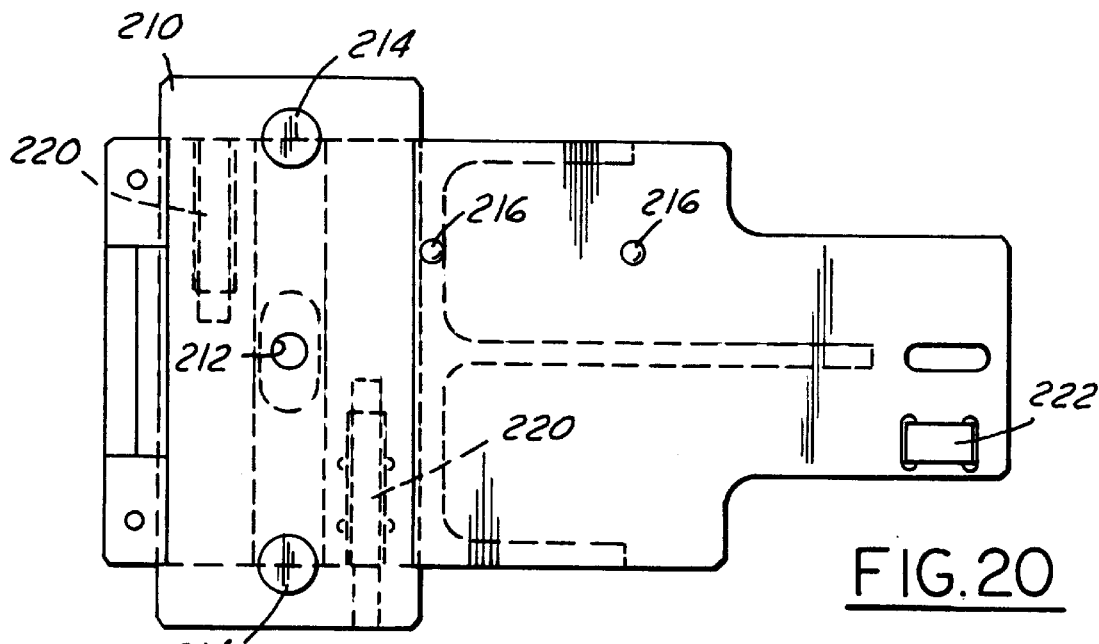
FIGS. 20 and 21 are respective top plan and side elevational views of a portion of the mounting arrangement illustrated in FIGS. 15–17.
Figure 21:
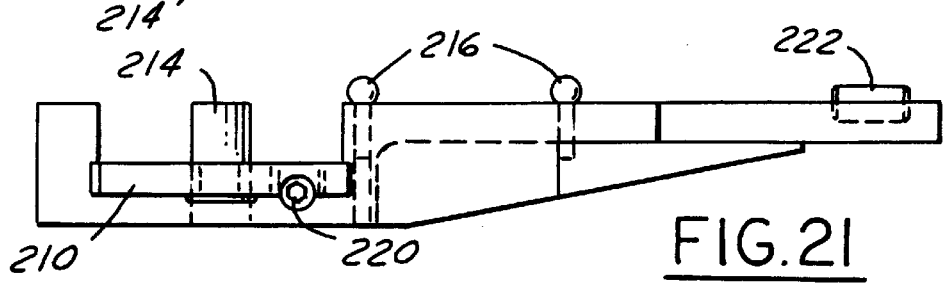

Clamp mounting plate 142 (FIGS. 18–21) secures apparatus 30 to headplate 92 (FIG. 9) through an internal adjustment plate 210, a screw 212 and two dowel pins 214 (FIG. 20). Apparatus 30 is located on clamp mounting plate 142 by two spherical pins 216 that engage slots 174, 176 in bottom plate 132, and is secured to the clamp mounting plate by the screws 218. Set screws 220, 222 are used to adjust apparatus 30 in the x and y directions (radial and tangential to the container and the axis of rotation of the starwheel conveyor) relative to the exact position of the axis of container 32 at the test station. For containers of ⅝ inch to three inches finish diameter, spherical pins 216 in the clamp mounting plate are positioned in slots 174 and 176 of bottom plate 132. For containers larger than three inches diameter, spherical pins 216 in the clamp mounting plate are positioned in slots 172, 174 of bottom plate 132.

There have thus been disclosed an apparatus and method for inspecting the finish of containers, particularly for detecting horizontal and vertical checks in the finish of translucent containers, that fully satisfy all of the objects and aims previously set forth. Both vertical and horizontal checks are detected at a single inspection station. Adjustment of the apparatus for containers of differing finish diameters may be readily and rapidly accomplished in a user-friendly manner. The optical system provides enhanced ranges for detection of both horizontal and vertical checks, as well as opportunity for discrimination between checks and other container finish variations. Knowledge of horizontal and vertical checks, blisters, split seams and offset seams is valuable for identifying the different types of variations for classifying rejects, and for controlling the container forming process whether or not the container is rejected. The use of fresnel lenses on both the light sources and the light sensors eliminates spherical aberrations, while the use of scheimpflug lens arrangements maintain focus of the various sensors in spite of angular viewing of the illuminated container finish areas. The various aspects of the invention most preferably are used in combination with each other. However, the aspects of the invention, such as the simultaneous position-adjustment feature of the invention, may be readily used in optical inspection situations involving inspection for other than finish checks.

The invention has been described in conjunction with the presently preferred embodiment thereof, and various modifications and variations have been described. Other modifications and variations will readily suggest themselves to persons of ordinary skill in the art in view of the foregoing description. The invention is intended to embrace all such modifications and variations as fall within the spirit and broad scope of the appended claims.

What is claimed is:

1. Apparatus for detecting checks in the finish of a translucent container having a central axis and an open mouth, which comprises:

means at an inspection station for rotating the container about its axis, a first light source for directing first light energy onto a first portion of the container finish as it rotates, a first light sensor disposed with respect to said first light source and the container finish at said inspection station to receive portions of said first light energy reflected from horizontal checks in the container finish, a second light source for directing second light energy onto a second portion of the container finish as it rotates, a second light sensor disposed with respect to said second light source and the container finish at said inspection station to receive portions of said second light energy reflected from vertical checks in the container finish, and an information processor coupled to said first and second sensors for detecting horizontal and vertical checks in the container finish as a function of said reflected portions of said first and second light energies, wherein said information processor comprises means for scanning said first and second sensors at increments of container rotation, and means for determining angular position of variations at the container finish that reflect light energy onto said first and second sensors.

2. The apparatus set forth in claim 1 wherein said information processor further includes means for distinguishing check variations at the container finish at which light from said first light source is reflected onto said first sensor or light from said second light source is reflected onto said second sensor, but not both, from blister variations at which light from said first source is reflected onto said first sensor and light from said second source is reflected onto said second sensor.

3. The apparatus set forth in claim 1 wherein said first and second sensors comprise linear array sensors, and wherein said information processor includes means for scanning said linear array sensors at increments of container rotation.

4. The apparatus set forth in claim 3 wherein said first and second light sources simultaneously direct said first and second light energies onto respectively different areas of the container finish.

5. The apparatus set forth in claim 4 wherein said first and second light sources illuminate respective rectangular areas of the container finish.

6. The apparatus set forth in claim 5 wherein each of said linear array sensors has a linear field of view disposed within the rectangle of illumination from the associated light source.

7. The apparatus set forth in claim 4 wherein one of said second light source and said second light sensor is disposed above the container mouth and the other of said second light source and said second light sensor is disposed beneath the container mouth of the container at said station.

8. The apparatus set forth in claim 7 wherein one of said second light source and said second sensor is disposed in opposition to an external surface of the container finish, and the other of said second light source and said first sensor is disposed in opposition to the inside surface of the container finish through the container mouth.

9. The apparatus set forth in claim 4 wherein said first light source and said first sensor are disposed above the container mouth in a plane that includes the container axis.

10. The apparatus set forth in claim 9 wherein one of said first light source and said first sensor is disposed in opposition to an external surface of the container finish, and the other of said first light source and said first sensor is disposed in opposition to the inside surface of the container finish through the container mouth.

11. The apparatus set forth in claim 10 wherein one of said second light source and said second light sensor is disposed above the container mouth, and the other of said second light source and said second sensor is disposed below the container mouth.

12. The apparatus set forth in claim 9 further comprising a third light source for directing third light energy onto a third portion of the container finish as it rotates, and a third light sensor disposed with respect to said third light source and the finish of the container at said inspection station to receive portions of said third light energy reflected from vertical checks in the container finish, said information processor being coupled to said third sensor for detecting vertical checks in the container finish as a function of reflected portions of said third light energy, said second and third light sources being disposed on opposite sides of said plane, and said second and third light sensors being disposed on opposite sides of said plane from each other and from the associated light source.

13. The apparatus set forth in claim 6 wherein said first light source and said first sensor are mounted in a first optical subassembly, wherein said second light source and said second sensor are mounted in a second optical subassembly, and wherein said apparatus further comprises means mounting said first and second optical subassemblies to each other.

14. The apparatus set forth in claim 13 wherein said means mounting said first and second optical subassemblies to each other includes means for simultaneously adjusting said first and second optical subassemblies with respect to each other and with respect to said station to accommodate container finishes of differing diameters.

15. The apparatus set forth in claim 14 further comprising a third light source for directing third light energy onto a third portion of the container finish as it rotates, a third light sensor disposed with respect to said third light source and the finish of the container at said inspection station to receive portions of said third light energy reflected from vertical checks in the container finish, and means mounting said third light source and said third sensor in a third optical subassembly, and wherein said means mounting said first and second optical subassemblies also mounts said third optical subassembly for simultaneous adjustment of said first, second and third optical subassemblies with respect to each other and with respect to said inspection station to accommodate container finishes of differing diameters.

16. The apparatus set forth in claim 6 wherein said first and second sensors further comprise associated fresnel lenses, said linear array sensors and said associated fresnel lenses being disposed in a scheimpflug arrangement with the opposing surface of the container finish.

17. The apparatus set forth in claim 6 wherein said rectangular areas have long dimensions parallel to the container axis and covering the entire container finish.

18. The apparatus set forth in claim 6 wherein said first and second light sources comprise a common source of light energy, and first and second fiber optic bundles extending from said common source to illuminate said first and second portions of the container finish.

19. Apparatus for detecting checks in the finish of a translucent container having a central axis and an open mouth, which comprises:

means at an inspection station for rotating the container about its axis, a first light source for directing first light energy onto a first portion of the container finish as it rotates, a first light sensor disposed with respect to said first light source and the finish of the container at said inspection station to receive portions of the first light energy reflected from vertical checks in the container finish, a second light source for directing second light energy onto a second portion of the container finish as it rotates, a second light sensor disposed with respect to said second light source and the finish of the container at the inspection station to receive portions of the second light energy reflected from vertical checks in the container finish, and an information processor coupled to said first and second sensors for detecting vertical checks in the container finish, said first and second light sources being disposed in opposite sides of the container finish, and said first and second sensors being disposed on sides of the container finish opposite from each other and from the associated light source, such that said sensors and said information processor detect vertical checks at a range of angles on both sides of a radial check angle, said information processor comprising means for scanning said first and second sensors at increments of container rotation, and means for determining angular positions of variations at the container finish that reflect light energy onto said first and second sensors.

20. The apparatus set forth in claim 19 wherein said first and second sensors comprise linear array sensors, and wherein said information processor includes means for scanning said linear array sensors at increments of container rotation.

21. The apparatus set forth in claim 20 wherein said first and second light sources simultaneously direct said first and second light energies onto respectively different areas of the container finish.

22. The apparatus set forth in claim 21 wherein said first and second light sources illuminate respective rectangular areas of the container finish.

23. The apparatus set forth in claim 22 wherein each of said linear array sensors has a linear field of view disposed within the rectangle of illumination from the associated light source.

24. The apparatus set forth in claim 23 wherein said first and second light sources are disposed on one side of the container finish either above or below the container mouth, and wherein said first and second sensors are disposed on the other side of the container mouth.

25. The apparatus set forth in claim 24 wherein either said first and second light sources or said first and second sensors are disposed in opposition to an external surface of the container finish, and the other of said first and second light sources and the first and second sensors are disposed in opposition to the inside surface of the container finish through the container mouth.

26. The apparatus set forth in claim 25 wherein said first light source and said first sensor are mounted in a first optical subassembly, wherein said second light source and said second sensor are mounted in a second optical subassembly, and wherein said apparatus further comprises means mounting said first and second optical subassemblies to each other.

27. The apparatus set forth in claim 26 wherein said means mounting said first and second optical subassemblies to each other includes means for simultaneously adjusting said first and second optical subassemblies with respect to each other and with respect to said station to accommodate container finishes of differing diameters.

28. The apparatus set forth in claim 27 further comprising a third light source for directing third light energy onto a third portion of the container finish as it rotates, a third light sensor disposed with respect to said third light source and the finish of the container at said inspection station to receive portions of said third light energy reflected from horizontal checks in the container finish, and means mounting said third light source and said third sensor in a third optical subassembly, and wherein said means mounting said first and second optical subassemblies also mounts said third optical subassembly for simultaneous adjustment of said first, second and third optical subassemblies with respect to each other and with respect to said inspection station to accommodate container finishes of differing diameters.

29. The apparatus set forth in claim 25 further comprising a third light source for directing third light energy onto a third portion of the container finish as it rotates, and a third light sensor disposed in a plane with respect to said third light source and the finish of the container at said inspection station to receive portions of said third light energy reflected from horizontal checks in the container finish, said information processor being coupled to said third sensor for detecting horizontal checks in the container finish as a function of reflected portions of said third light energy, said first and second light sources being disposed on opposite sides of said plane, and said first and second light sensors being disposed on opposite sides of said plane from each other and from the associated light source.

30. The apparatus set forth in claim 25 wherein said first and second sensors further comprise associated fresnel lenses, said linear array sensors and said associated fresnel lenses being disposed in a scheimpflug arrangement with the opposing surface of the container finish.

31. The apparatus set forth in claim 23 wherein said rectangular areas have long dimensions parallel to the container axis and covering the entire container finish.

32. The apparatus set forth in claim 23 wherein said first and second light sources comprise a common source of light energy, and first and second fiber optic bundles extending from said common source to illuminate said first and second portions of the container finish.

33. A method of detecting checks in the finish of a translucent container that comprises the steps of:

(a) rotating the container about its central axis, (b) simultaneously directing first and second light energies onto differing portions of the container finish as it rotates, (c) positioning first and second light sensors to receive portions of said first and second light energies, respectively, reflected from checks in the container finish, said first light sensor being oriented with respect to said first light source and the container finish for receiving portions of said first light energy reflected from horizontal checks in the container finish, and said second light sensor being oriented with respect to said second light source and the container finish for receiving portions of said second light energy reflected from vertical checks in the container finish, (d) detecting horizontal and vertical checks in the container finish as a function of said first and second light energies reflected onto said sensors, (e) distinguishing among: (i) horizontal checks in the container finish from which light is reflected from said first source onto said first sensor, but not light from said second source onto said second sensor, (ii) vertical checks in the container finish from which light is reflected from said second source onto said second sensor, but not light from said first source onto said first sensor, and (iii) bubbles in the container finish from which light is reflected from both said first and second sources onto the associated sensors.

34. Apparatus for inspecting the finish of a container having a central axis and an open mouth, which comprises:

means at an inspection station for rotating the container about its axis such that said mouth is disposed in a horizontal plane, a first light source for directing light energy onto the finish of a container as it rotates, a first light sensor disposed with respect to said first light source and the container to receive light energy from said first source after interaction with the container finish, a second light source for directing light energy onto the finish of a container as it rotates, a second light sensor disposed with respect to said second light source and the container to receive light energy from said second source after interaction with the container finish, first means mounting said first light source and said first light sensor in a first optical subassembly, second means mounting said second light source and said second light sensor in a second optical subassembly, and means mounting said first and second optical subassemblies to each other at said inspection station, including means for simultaneously adjusting said first and second optical subassemblies with respect to each other and with respect to said station to accommodate container finishes of differing diameters.

35. The apparatus set forth in claim 34 wherein said first optical subassembly includes a first plate and first bracketry mounting said first source and said first sensor on said first plate, wherein said second optical subassembly includes a second plate and second bracketry mounting said second source and said second sensor on said second plate, and wherein said simultaneously adjusting means comprises a pin on one of said first and second plates and a slot on the other of said first and second plates such that motion of said first plate in one linear direction moves said second plate in a second linear direction at an angle to said first direction.

36. The apparatus set forth in claim 35 wherein said mounting means comprises a base plate for mounting in fixed position at said inspection station, and means slidably mounting said first and second plates on said base plate.

37. The apparatus set forth in claim 36 further comprising a bridge plate mounted on and spaced from said base plate, said first plate being slidably mounted on said bridge plate for motion in said first direction, and said second plate being mounted between said bridge plate and said base plate for motion in said second linear direction.

38. The apparatus set forth in claim 37 further comprising: a third light source for directing light energy onto the finish of a container as it rotates at said inspection station, and a third light sensor disposed with respect to said third light source and the container to receive light energy from the third light source after interaction with the container finish, third means mounting said third light source and said third light sensor in a third optical subassembly, said third optical subassembly including a third plate and third bracketry mounting said third light source and third sensor on said third plate, said third plate being mounted between said bridge plate and said base plate for motion in a third linear direction at an angle to said first direction equal and opposite to said second direction.

39. The apparatus set forth in claim 38 wherein said second and third plates have first slots that extend in said second and third linear directions respectively, and wherein said first plate has a pin that extends into both of said first slots in said first and second plates.

40. The apparatus set forth in claim 39 wherein said second and third plates have second slots that extend perpendicular to said first direction, and pins on each said second and third plate extending into the second slot on the other, such that said second and third plates move linearly perpendicular to said first direction with respect to each other, and linearly in said second and third directions with respect to said first plate.

41. The apparatus set forth in claim 40 wherein said simultaneously adjusting means further comprises a leadscrew rotatably carried by said bridge plate and operatively coupled to said first plate, and a knob on said leadscrew for rotating said leadscrew.

42. The apparatus set forth in claim 41 further comprising a lock carried by said bridge plate for locking said leadscrew in adjusted position.

43. The apparatus set forth in claim 40 wherein each said bracketry in said first, second and third optical subassemblies includes means for adjusting position and angle of the associated light source and sensor with respect to each other.

44. Apparatus for detecting checks in the finish of a translucent container having a central axis and an open mouth, which comprises:

means at an inspection station for rotating the container about its axis with said mouth in a horizontal plane, a first optical subassembly comprising a first light source for directing first light energy onto a first portion of the container finish as it rotates, a first light sensor to receive portions of said first light energy reflected from horizontal checks in the container finish, a first plate, and first bracketry mounting said first light source and said first sensor on said first plate, a second optical subassembly comprising a second light source for directing second light energy onto a second portion of the container finish as it rotates, a second light sensor to receive portions of said second light energy reflected from vertical checks in the container finish, a second plate, and second bracketry mounting said second light source and said second sensor on said second plate, a third optical subassembly comprising a third light source for directing third light energy onto a third portion of the container finish as it rotates, a third light sensor to receive portions of said third light energy reflected from vertical checks in the container finish, a third plate, and third bracketry mounting said third light source and said third light sensor on said third plate, means mounting said first, second and third optical subassemblies to each other at an inspection station, with said first light source and said first sensor being disposed in a vertical plane, with said second and third light sources on opposite sides of said vertical plane, and with said second and third light sources disposed in opposite sides of said vertical plane from each other and from the associated light source, means on said mounting means cooperable with said plates for adjusting said first optical subassembly in a first direction said vertical plane, and simultaneously adjusting said second and third optical subassemblies in second and third directions at equal and opposite angles to said first direction, and an information processor coupled to said first, second and third sensors for detecting horizontal and vertical checks in container finish.

45. The apparatus set forth in claim 44 wherein said mounting means comprises a base plate for mounting in fixed position at said inspection station, and means slidably mounting said first, second and third plates on said base plate.

46. The apparatus set forth in claim 45 further comprising a bridge plate mounted on and spaced from said base plate, said first plate being slidably mounted on said bridge plate for motion in said first direction, and said second and third plates being mounted between said bridge plate and said base plate for motion in said second and third directions.

47. The apparatus set forth in claim 46 wherein said second and third plates have first slots that extend in said second and third directions respectively, and wherein said first plate has a pin that extends into both of said slots in said first and second plates.

48. The apparatus set forth in claim 47 wherein said second and third plates have second slots that extend perpendicular to said first direction, and pins on each said second and third plate extending into the second slot on the other, such that said second and third plates move linearly perpendicular to said first direction with respect to each other, and linearly in said second and third direction with respect to said first plate.

49. The apparatus set forth in claim 48 wherein said simultaneously adjusting means further comprises a leadscrew rotatably carried by said bridge plate and operatively coupled to said first plate, and a knob on said leadscrew for rotating said leadscrew.

50. The apparatus set forth in claim 49 further comprising a lock carried by said bridge plate for locking said leadscrew in adjusted position.

51. The apparatus set forth in claim 48 wherein each said bracketry in said first, second and third optical subassemblies includes means for adjusting position and angle of the associated light source and sensor with respect to each other.

52. The apparatus set forth in claim 45 wherein said information processor further includes means for distinguishing check variations at the container finish at which light from said first light source is reflected onto said first sensor, or light from said second or third light source is reflected onto the associated sensor, but not both, from blister variations at which light from said first source is reflected onto said first sensor, light from said second source is reflected onto said second sensor and light from said third source is reflected onto said third sensor.

* * * * *